US 6,195,585 B1

(12) United States Patent
Karunasiri et al.

(10) Patent No.: US 6,195,585 B1
(45) Date of Patent: Feb. 27, 2001

(54) REMOTE MONITORING OF IMPLANTABLE COCHLEAR STIMULATOR

(75) Inventors: Rankiri Tissa Karunasiri, Van Nuys, CA (US); Charles C. Finley, Research Triangle Park, NC (US)

(73) Assignee: Advanced Bionics Corporation, Sylmar, CA (US)

( * ) Notice: Subject to any disclaimer, the term of this patent is extended or adjusted under 35 U.S.C. 154(b) by 0 days.

(21) Appl. No.: 09/344,429

(22) Filed: Jun. 25, 1999

Related U.S. Application Data

(60) Provisional application No. 60/090,820, filed on Jun. 26, 1998.

(51) Int. Cl.[7] .................................................. A61N 1/36
(52) U.S. Cl. .................................................. 607/57
(58) Field of Search .......................... 607/55, 57, 60, 607/28, 32

(56) References Cited

U.S. PATENT DOCUMENTS

| 4,991,582 | 2/1991 | Byers et al. | 128/419 |
| 5,531,774 | 7/1996 | Schulman et al. | 607/56 |
| 5,626,629 | 5/1997 | Faltys et al. | 607/57 |
| 5,758,651 | 6/1998 | Nygard et al. | 128/741 |

FOREIGN PATENT DOCUMENTS 9906108  2/1999  (WO).

OTHER PUBLICATIONS

Finley, et al., "Speech Processors for Auditory Prostheses", Research Triangle Institute Ninth Quarterly Progress Report (30 pages) 1997.

*Primary Examiner*—Scott M. Getzow
(74) *Attorney, Agent, or Firm*—Bryant R. Gold

(57) ABSTRACT

Monitoring/measurement circuitry within an implantable stimulator, e.g., an implantable cochlear stimulator (ICS), includes a first analog multiplexer (MUX) connected to a gain controlled, low noise, differential amplifier. The output of the differential amplifier is coupled to a second analog MUX along with other analog signals, e.g., operating or bias voltages used within the implantable stimulator. The signal appearing at the output of the second analog MUX is preliminary processed as required, e.g., to adjust the amplitude (attenuate) and/or filter out high frequency components. Once processed, the signal is then digitized in an analog-to-digital (A/D) converter. The digitized signal is then stored in memory as measured data, and eventually transmitted to a remote (non-implanted) processor for further processing, analysis, examination and/or feedback. Such monitoring/ measurement circuitry may operate in a low power mode for frequent monitoring of certain signals selected by the second analog MUX, and a high power mode for less frequent monitoring of other signals, e.g., an evoked potential, selected by the first analog MUX. When sensing an evoked response, all signal activity associated with an applied stimulus, including the artifact and the evoked response, may be sensed, monitored, preliminarily processed, and stored in real time, and then subsequently telemetered to the remote signal processing device. The remote signal processing device may then apply additional signal processing to the received data, including removal of the artifact from the evoked response, thereby allowing the evoked response to be identified and analyzed and used.

20 Claims, 8 Drawing Sheets

REMOTE MONITORING OF IMPLANTABLE COCHLEAR STIMULATOR

The present application claims the benefit of U.S. Provisional Application Ser. No. 60/090,820; filed Jun. 26, 1998, which application is incorporated herein by reference.

BACKGROUND OF THE INVENTION

The present invention relates to implantable medical devices, and more particularly to implantable medical devices that stimulate the neural system (referred to hereafter as a "neural stimulator" or simply as a "stimulator"). Even more particularly, the invention relates to a neural stimulator that measures and collects data resulting from neural stimulation, and transmits the collected data to a processor for analysis, storage, reporting and/or other purposes. The processor that receives the collected data may be at a non-implanted location remote from the stimulator, at an implanted location adjacent the stimulator, or incorporated as additional circuitry within the same implantable housing as the stimulator.

In an implantable medical device, particularly an implantable neural stimulator, there is a need to measure internal voltages, determine electrode impedances, determine output stimulus linearity, sense and measure biological responses to an electrical impulse, as well as to monitor and measure other biological activities that are associated with or occur coincident with the operation of the device.

Disadvantageously, due to the limited power available within an implantable medical device, coupled with the presence of digital and RF noise in or in the near proximity of the device, the design of any monitoring and sensing circuitry within such device must be non-traditional.

For example, in order to measure a biological response to an applied stimulus (i.e., an "evoked response"), there is a need to deal with the presence of the stimulus artifacts which accompany any applied stimulus. Having the capability of sensing and monitoring the evoked response to an applied stimulus provides a very valuable tool for setting the stimulus parameters at an appropriate level for a given patient. However, heretofore there has been little success in sensing the evoked response because it is such a small signal compared to the stimulus artifact.

By way of example, an evoked response within the aural nerve region may only be in the 10 to 500 microvolt ($\mu v$) range. The needed amplification for handling such small signals (which amplification must be on the order of about 1000) makes the amplifier recovery from the artifacts too slow to capture the evoked response, which evoked response onset typically occurs about 30 to 40 microseconds ($\mu s$) after the stimulus is applied.

In U.S. Pat. No. 5,531,774 there is disclosed a multichannel cochlear stimulation system of the type with which the present invention may be used. As shown in the '774 patent, the system therein disclosed includes both external (non-implanted) and implanted portions. The implanted portion comprises an implantable cochlear stimulator (ICS) integrally attached to a cochlear electrode array. The electrode array includes a multiplicity, e.g., sixteen, spaced-apart electrodes that may be inserted into a human cochlea, any one of which may be activated for application of an electrical stimulus to cochlear tissue. The ICS disclosed in the '774 patent further includes a back telemetry circuit which allows certain measurements, e.g., voltage levels present within the ICS, or other measured parameters, to be sent back to the external portion of the system. The ICS disclosed in the '774 patent is incorporated herein by reference.

In U.S. Pat. No. 5,758,651, there is disclosed a system whereby the sensing electrodes are open circuited for a selected period of time following delivery of a stimulus in order to avoid sensing the artifact. Disadvantageously, the selected period of time during which the electrodes are open circuited varies from patient to patient, and may vary for a given patient depending upon other conditions. Further, switching circuitry is required to perform the open-circuiting function, which switching may introduce switching transients and glitches into the signal.

Thus, it is seen that there is a need for monitoring circuitry within an implantable neural stimulator, e.g., an implantable cochlear stimulator, that is able to accurately sense the evoked response in the presence of large stimulus artifacts, which stimulus artifacts typically vary in terms of amplitude and duration.

SUMMARY OF THE INVENTION

The present invention addresses the above and other needs by providing monitoring/measurement circuitry within an implantable stimulator, e.g., an implantable cochlear stimulator, that allows several different analog measurements to be selectively monitored from within the implantable stimulator, including electrode impedance, evoked responses, and the like. Such measurements are processed, as required, digitized, and stored in the implantable stimulator. When needed or upon request, the measured data is telemetered, or otherwise transferred or sent, from the implant device to a remote processing device. The remote processing device is typically an external (non-implanted) programmer device and/or personal computer (PC). However, it is to be understood that the remote processing device may also comprise an implantable processor that is electrically coupled with the implantable stimulator (e.g., as in the case of a fully implantable cochlear stimulator system of the type disclosed in U.S. patent application Ser. No. 09/126,615, filed Jul. 31, 1998; or Ser. No. 60/108,923, filed Nov. 17, 1998; both of which applications are incorporated herein by reference); or a processor that comprises additional circuitry housed within the same implantable housing as the implantable stimulator (e.g., as in the case of a single package, fully implantable processor/stimulator). Storage of the data in the implantable stimulator further allows the memory within the implantable stimulator to act as a buffer so that data obtained in real-time at a rapid rate can be transmitted to the remote processor at a slower rate, commensurate with the bandwidth of the telemetry or other data link.

In accordance with an important aspect of the invention, all signal activity associated with an applied stimulus, including the artifact, the evoked response and/or the compound action potential (CAP), may be sensed, monitored, preliminarily processed, and stored in real time using circuitry contained within the implantable stimulator; and then subsequently telemetered or sent to a remote signal processing device. The remote signal processing device may then apply additional processing to the received data, including removal of the artifact from the evoked response or CAP, thereby allowing the evoked response and/or CAP to be analyzed, and/or used as feedback information to assist in setting of the stimulus parameters.

In accordance with another aspect of the invention, the measuring/monitoring circuitry of the present invention includes two-level multiplexing of analog signals. Advantageously, two levels of analog multiplexing allow a low power mode for performing frequent measurements with rapid ON/OFF capability, and a high performance mode for performing less frequent Evoked Potential and other electrode-related measurements.

In order to reduce the static power consumption of the measuring/monitoring circuitry of the present invention, it is a feature of the invention that each block in the measuring/monitoring circuitry may be selectively turned OFF or powered down.

The measuring/monitoring circuitry of the invention includes a first analog multiplexer (MUX) connected to a gain controlled, low noise, differential amplifier. The output of the differential amplifier is coupled to a second analog MUX along with other analog signals, e.g., operating or bias voltages used within the device. The signal appearing at the output of the second analog MUX is preliminary processed as required, e.g., to adjust the amplitude (attenuate) and/or filter out high frequency components. Once processed, the signal is then presented to an analog-to-digital (A/D) converter where it is sampled at a specified rate and digitized. The digitized signal is then stored in memory, and eventually transmitted to a remote, e.g., non-implanted, processor for further processing, analysis and examination.

Different fundamental operating modes may be used with the measuring/monitoring circuitry. In a first operating mode, for example, the second analog MUX, a voltage divider (attenuator) circuit, and the A/D converter are all activated. This mode allows internal operating voltages used within the implantable stimulator, which are applied as inputs to the second analog MUX, to be readily monitored. In a second operating mode, all blocks of the measuring/monitoring circuitry are activated, thereby allowing electrode-related measurements, including evoked response measurements, to be made. Such measurements include, but are not limited to, evoked potential determinations, stapedius reflex measurements, electrode impedance measurements, and stimulus and/or electric field strength measurements. In a third operating mode, designated blocks of the measuring/monitoring circuitry are activated, as needed, allowing key measurements to be made that are immediately used, e.g., as closed loop feedback information, to control the characteristics of the electrical stimuli delivered by implantable stimulator.

Different measurements made by the monitoring circuitry of the present invention may require a different gain setting in the signal path. Advantageously, such different gain settings are readily achieved using the gain controlled differential amplifier connected to the output of the first analog MUX and/or the switched in attenuator connected to the output of the second analog MUX. Further, different measurements are made possible through the use of the first analog MUX, which allows any electrode pair, for example, to be selectively coupled to the gain controlled differential amplifier.

An important feature of the present invention is that when sensing evoked potentials between a selected pair of electrodes, the differential amplifier recovers quickly and symmetrically from saturation, and its gain is controlled to operate the amplifier in a linear region for the signals of interest. In this way, there is no need to blank the signal path, e.g., open circuit the signal path, during application of the stimulus, thereby avoiding switching transients or signal glitches that could easily be mistaken for bio signals.

Another feature of the invention, when measuring evoked potentials between a selected pair of electrodes, is that a stream of multiphasic stimulus pulses, e.g., biphasic stimulus pulses, having alternating positive leading and negative leading phases, is applied to the selected electrode pair. The resulting response is then averaged, e.g., using a remote processing device, which averaging tends to cancel out induced signals, leaving only the desired bio signals for analysis.

Still a further feature of the invention, when operating in an electrode-related measurement mode, is that any two electrodes, including one or more reference electrodes, may be paired as "sense" electrodes in order to make a desired differential measurement between the selected pair of sense electrodes. This means, for example, that the reference electrode used for a given measurement may be readily switched from the case band to any other electrode.

It is thus an object of the present invention to provide a measurement/monitoring circuit for use within an implantable stimulator that facilitates sensing the evoked response to an applied stimulus.

It is a further object of the invention to provide such a measurement/monitoring circuit that is programmable, meaning that the types of signals and/or measurements that are to be measured, including the electrode pairing through which evoked or other electrode-related measurements are sensed, can be readily selected.

It is another object of the invention to provide a measurement/monitoring circuit that operates at minimal operating power.

BRIEF DESCRIPTION OF THE DRAWINGS

The above and other aspects, features and advantages of the present invention will be more apparent from the following more particular description thereof, presented in conjunction with the following drawings wherein.

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

Figure 1A:
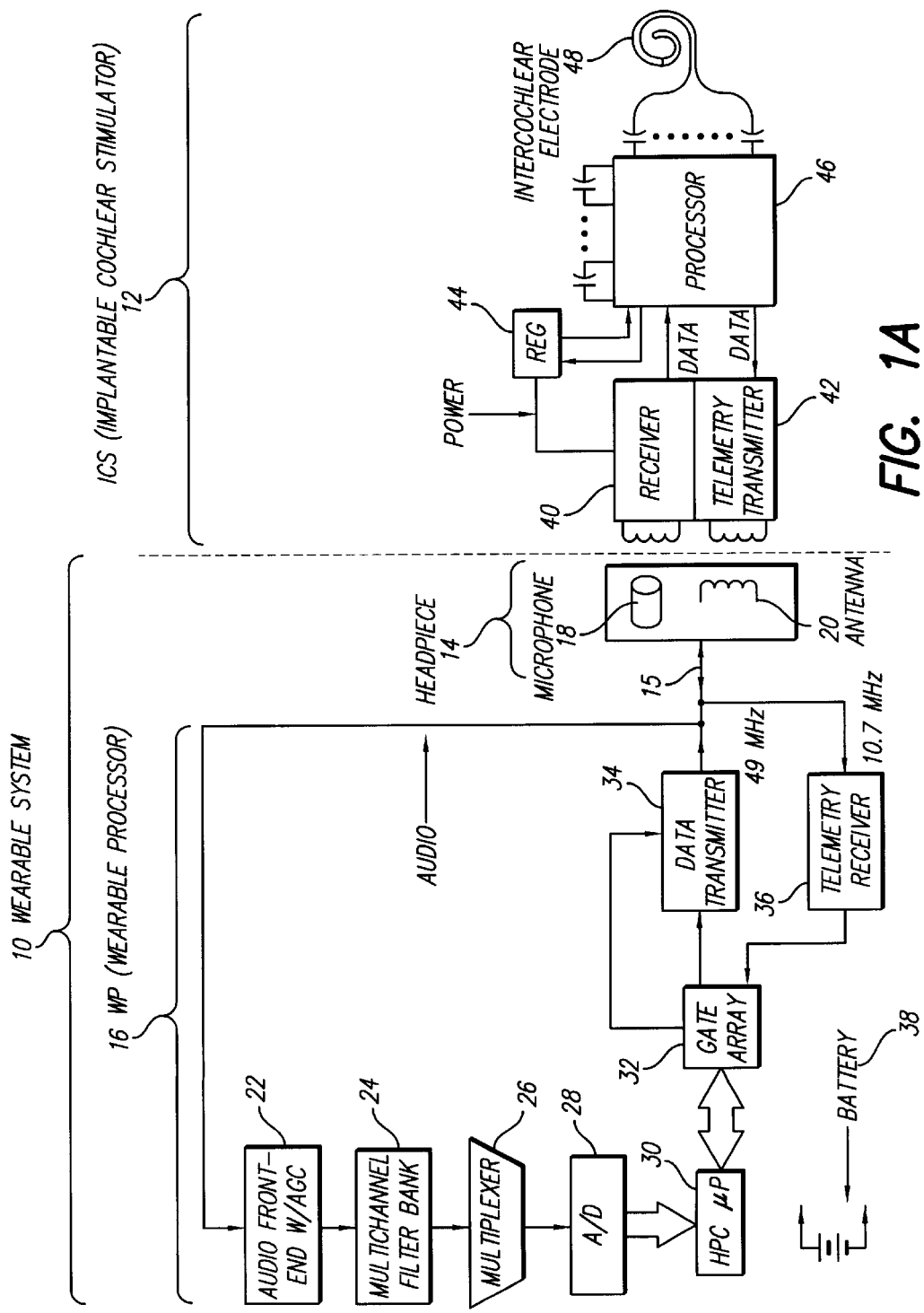
FIG. 1A is a functional block diagram of a typical implantable tissue stimulator system.

To better appreciate and understand the function performed by the present invention, it will first be helpful to have a general overview of a typical implantable stimulator of the type with which the present invention may be used. To that end, reference is made to FIG. 1, where there is shown a functional block diagram of a typical implantable tissue stimulator system. The tissue stimulator system shown in FIG. 1 is of the same type disclosed in the '774 patent, previously referenced. Such system includes both external (non-implanted) and implanted portions. The external portion comprises a wearable system 10 that includes a headpiece 14 and a wearable processor 16. The implanted portion comprises an implantable cochlear stimulator (ICS) 12. It is to be understood that while an implantable cochlear stimulator, or ICS, represents a preferred type of stimulator with which the invention may be used, the invention may also be used with other types of tissue or nerve stimulators. Any implantable stimulator (implant device) which has a multiplicity of electrodes, and which has internal circuitry and parameters that need monitoring, and which has a backward telemetry channel or other data link (for sending information from the implantable stimulator to a remote location), or which may use the information sensed and sent or telemetered back to the remote device in a feedback loop so as to better control stimulus parameters, may benefit from the invention.

As thus illustrated in FIG. 1, a basic cochlear stimulation system with which the present invention may be used includes an externally wearable system 10 and an implantable cochlear stimulator (ICS) 12. The external system 10 comprises a headpiece 14 and an externally wearable processor (WP) 16. The headpiece may be worn behind the ear of a hearing impaired person and comprises a conventional microphone 18 and an antenna 20 for transmitting and receiving electromagnetic energy preferably in the form of radio frequency signals. Such coupling may be restricted to magnetic field coupling only through the use of an electrostatic shield placed around the coils comprising the antenna 20. In addition, signals being sent from the ICS to the WP on one carrier frequency, as well as signals being sent from the WP to the ICS on another carrier frequency, may be transferred via a single coaxial cable 15 between the headpiece 14 and the WP 16. This can be accomplished by having tuned inductor-capacitor filters for each frequency at each end of the coaxial cable.

Still referring to FIG. 1, the WP 16, powered by a battery 38 or other suitable power source, is adapted to receive audio signals received by the microphone 18 and to transmit such signals to conventional audio front end circuitry 22 which features automatic gain control (AGC). The audio signals processed by the audio front end 22 are transmitted to a bank of filters 24 for filtering and for generation of a plurality of parallel audio signals. The audio signals are processed by a multiplexer 26 and converted to a series of digital signals by an A to D converter 28 for application to a microprocessor 30. The filter bank may also be implemented as a group of digital filters, for example in a digital signal processor integrated circuit. In this case the signal flow would be from the audio front end and AGC 22, through an anti-aliasing filter, to an analog to digital converter, then into a digital filter bank 24 and the general processing of microprocessor 30.

The output of the microprocessor 30 is coupled through a custom gate array 32 that converts data from the microprocessor into a serial bit stream going to a data transmitter 34. The gate array 32 also converts data from a telemetry receiver 36 and the microprocessor 30 to control the power level of and data generated by the data transmitter 34.

As further illustrated in FIG. 1, the ICS 12 includes a receiver 40 for receiving data transmissions from the wearable system 10. The ICS 12 further includes a telemetry transmitter 42 for transmitting ICS status-indicating signals and/or measured signals from the ICS 12 to the wearable system 10. For example, power level indicating signals transmitted by the telemetry transmitter 42 may be received by the telemetry transmitter 36 and processed in the microprocessor 30 and gate array 32 to generate signals controlling the power level of the transmissions from the transmitter 34 to the ICS 12, thereby providing a closed-loop system for optimizing the power levels of the transmission from the wearable system 10 to the ICS 12 and hence conserving the battery 38 and optimizing the voltages generated within the system 10. Such a system for optimizing power levels is described in more detail in U.S. Pat. No. 5,876,425, incorporated herein by reference.

In addition to the receiver 40 and transmitter 42, the ICS 12 includes a regulator 44 for receiving a power signal from the receiver 40 to energize a processor 46. Data signals from the receiver 40 are also transmitted to the processor 46 for processing to generate stimulation signals applied to one or more of a plurality of capacitor coupled electrodes carried in an intra-cochlear electrode array 48.

Generally speaking, in response to control or data signals from the WP16, the ICS processor 46 selectively monitors voltages of the electrodes and associated circuitry in the ICS processor 46 and generates ICS status-indicating and measured signals. For example, the ICS processor 46 monitors the voltage applied to the regulator 44, the impedance of the electrodes and other voltages within the processor to generate the status-indicating signals which are sent as data to the telemetry transmitter 42 for transmission to the wearable system 10.

More particularly, in the cochlea stimulating system shown in FIG. 1, the signals transmitted to the ICS 12 from the wearable system 10 include electrical power components. Such power component signals are processed (e.g., rectified) within the receiver 40 through the series regulator 44 to generate a voltage signal which powers the ICS processor 46. The ICS processor 46 selectively monitors the voltage applied to the series regulator and generates a status-indicating signal relative to such voltage which is transmitted by the telemetry transmitter 42 and received by the telemetry receiver 36. As previously stated, such information is utilized in the microprocessor 30 and gate array 32 of the WP 16 to control the power level of the transmissions from the data transmitter 34 to the ICS 12, thereby providing a type of feedback control of the power level.

In accordance with the teachings of the present invention, other information, in addition to the voltages within the ICS 12, may be monitored and telemetered back to the WP 16 or PC attached to the WP 16. Alternatively, such other information may be used internally within the ICS processor 46, and associated circuitry, to better control the operation of the ICS 12. For example, a stapedius response detected through a stapedius electrode in response to an applied stimulus of a known magnitude could be used to guide the adjustment of the level (magnitude) of the next applied stimulus. In this manner, the applied stimuli may be dynamically set to an appropriate level in order to elicit a desired stapedius response. Such other information may thus be used to provide feedback information to the processor circuits within the WP 16, or elsewhere (e.g., within the ICS processor 46), so that appropriate adjustments can be made, e.g., to dynamically adjust the amplitude of the stimulus signal that is to be applied to a given patient. Further, such information may provide useful feedback during a fitting session when the ICS is first implanted within a patient, or when adjustments are made thereto after implant, so that the patient is able to obtain maximum benefit from the operation of the system. A representative fitting system for use with an ICS is disclosed in U.S. Pat. No. 5,626,629, issued May 6, 1997, which patent is incorporated herein by reference.

Figure 1B:
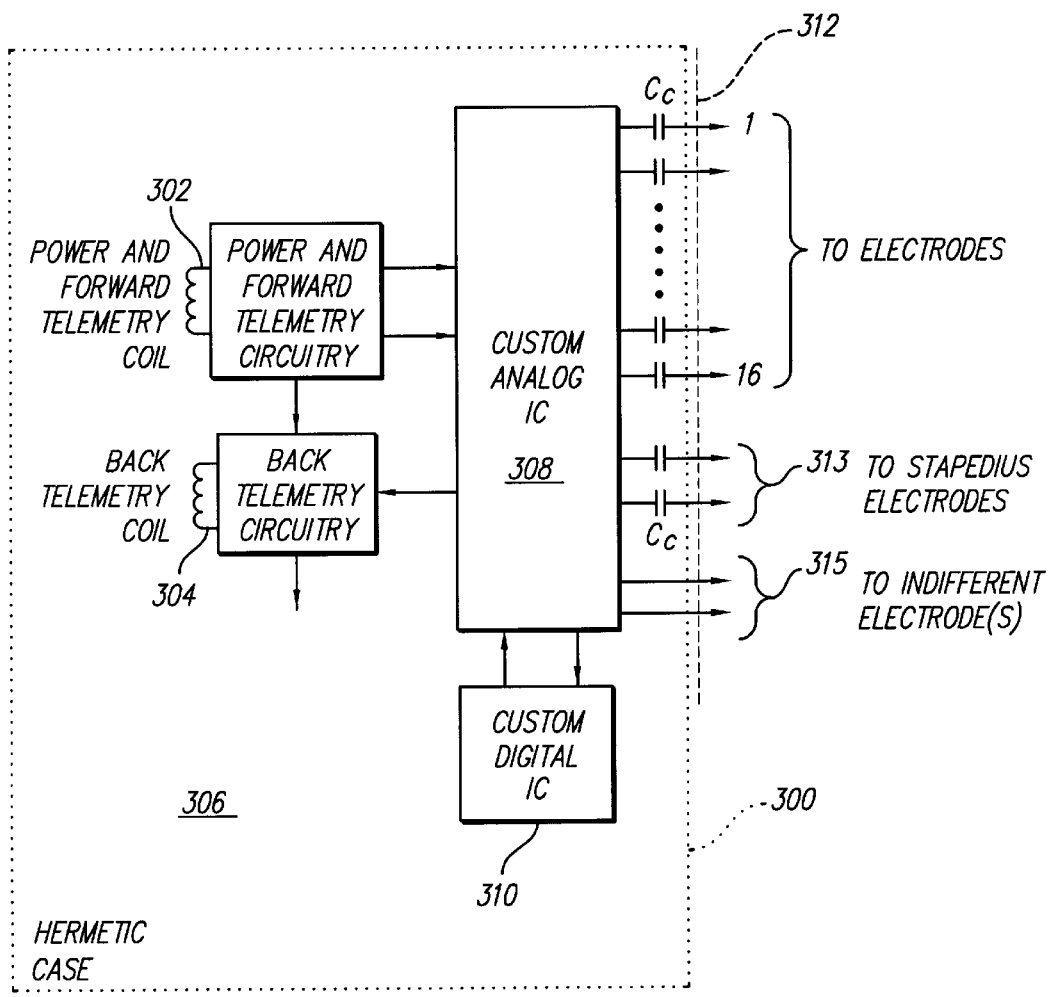
FIG. 1B depicts the physical partitioning of implantable cochlear stimulator (ICS) circuitry in accordance with a preferred embodiment of the invention.
Figures 1, 1C:
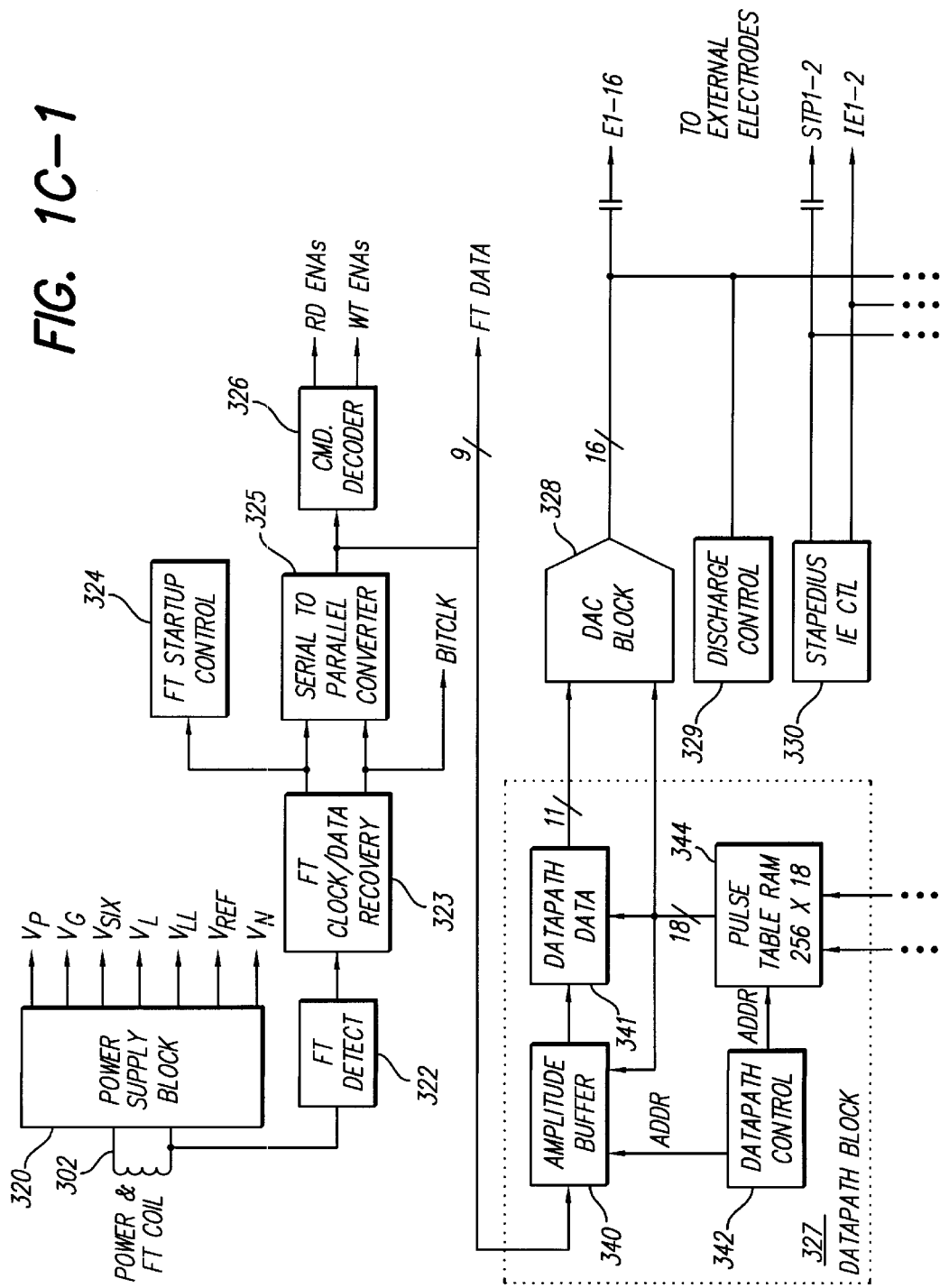
FIG. 1C shows the functional partitioning of the preferred ICS shown in FIG. 1B.

Turning to FIGS. 1B and 1C, a preferred implantable cochlear stimulator, or ICS, will next be described which includes the measurement and monitoring features embodied within the present invention. Such preferred ICS will hereafter be referred to as an ICS2 to distinguish it from a more conventional ICS of the type disclosed in '774 patent. The ICS2 comprises the implantable portion of a cochlear implant system which includes receiver/transmitter electronics, stimulation electronics, mechanical packaging, and an electrode array. The mechanical packaging and electrode array may be of conventional design, or as described in the referenced patent documents.

In operation, the ICS2 receives power and commands from an external unit in order to provide controlled, customizable current stimulus signals to the electrode array. In addition, the stimulator monitors internal voltages such as power supply levels and electrode potentials and transmits that information back to the external unit on demand.

The physical partitioning of the ICS2 is illustrated in FIG. 1B. As seen in FIG. 1B, the ICS2 includes electronic circuitry that fits inside a hermetically sealed, U-shaped ceramic case 300, e.g., of the type disclosed in U.S. Pat. No. 4,991,582, incorporated herein by reference. The package design may be the same as is used by ICS described in the '774 patent, previously referenced. The power and telemetry coils 302, and the back telemetry coil 304, and all circuitry are mounted on a ceramic hybrid 306 mounted inside the case 300. The majority of the circuitry is integrated into custom integrated circuits (ICs). Two IC's are typically employed—one analog IC 308 and one digital IC 310. Discrete components are used as necessary, e.g, coupling capacitors Cc. Attachment of the circuitry within the hermetically sealed case 300 to a multiplicity of external electrodes, e.g., sixteen electrodes, and to at least one indifferent (reference) electrode is through a bulkhead connector 312 at one end of the case. (Note that Electrodes are numbered 1 through 16, with 1 the most apical and 16 the most basal.) One or more additional indifferent electrodes 315 and at least two stapedius electrodes 313 may also be used with the ICS2, and are connected through the bulkhead connector 312 to the analog IC 308.

The functional partitioning of the ICS2 is shown in FIG. 1C. As seen in FIG. 1C, the ICS2 functionally includes a power supply block 320, a forward-telemetry (FT) detector 322, a FT Clock/Data Recovery circuit 323, a FT startup control circuit 324, a serial-to-parallel converter 325, a command decoder 326, a data path block 327, a digital-to-analog (DAC) block 328, a discharge control circuit 329, a stapedius/indifferent electrode control circuit 330, a voltmeter block 331, an implant identification block 332, a parallel-to-serial converter 333, a back telemetry (BT) oscillator and driver circuit 334, and an error and stimulation control circuit 335. It is the voltmeter block 331 wherein most of the circuitry associated with the present invention for the ICS2 is located. Hence, a more detailed description of the voltmeter block (referred to more accurately in connection with FIGS. 2–5 as a "Measuring and Monitoring Circuit") is presented below. However, before such presentation, it will also be helpful to have a brief overview of the other main functional components of the ICS2 shown in FIG. 1C.

Still referring to FIG. 1C, the Power Supply Block 320 receives an RF carrier signal, e.g., a 49 MHz signal, from the Power and Forward Telemetry (FT) Coil 302 and provides the following DC voltages to the ICS2:

$V_P$—The highest positive voltage used within the ICS2. It is normally set to: +6.6V to +16V above the IC substrate. This voltage is the positive analog supply.

$V_G$—This voltage is $V_P$ divided by two. This voltage functions as analog ground, and is normally at body potential.

$V_{SIX}$—A highly regulated voltage for use by an analog-to-digital (ADC). This voltage is typically set to +6 volts above the IC substrate.

$V_L$—A logic regulated supply for use by the analog chip, typically set to +3 volts above the IC substrate.

$V_{LL}$—A logic regulated supply for use by the digital chip, normally set to +1.8 volts above the IC substrate.

$V_{REF}$—A regulated voltage reference, designed to be +1.2 volts above the IC substrate.

$V_N$—The IC substrate level and digital ground.

The $V_P$ and $V_G$ levels are unregulated and are controlled externally by varying the power level of the RF carrier signal. The Power Supply Block also furnishes the power-on reset signal, which is active when $V_L$<2.25V (nom).

The Forward Telemetry (FT) Detector 322 receives the amplitude-modulated RF carrier signal (generated by the external or remote speech processor) from the coil 302 and outputs a logic-level 1.11 Mbit/sec FM-encoded serial data stream.

The FT Clock/Data Recovery circuit 323 takes the FM— (to be specific, biphase—mark—) encoded data stream and outputs a 1.11 MHz clock and the decoded serial data stream. The 1.11 Mhz clock is the main system clock (also known as BITCLK), and all timing is based on this clock.

The FT Startup Control circuit 324 monitors the decoded serial stream and determines when the phase-locked-loop (PLL) in the recovery circuit has achieved lock. (Lock time is approx. 100 usec.) The FT Startup Control waits for 200 usec. of correctly-decoded all-zeros startup pattern to determine that lock has occurred.

The Serial to Parallel Converter 325 receives the decoded FT serial data stream and packs the data into 12-bit words. This block also checks for odd parity in each 12-bit word. The lower 9 bits of this word can be used as amplitude or write-command data, depending on the particular command.

The command decoder 326 takes the parallel FT data, and decodes read and write commands to registers and memory in the ICS. In the case of write commands, 9 bits of the FT data are written into a selected register or memory location, for initialization and control purposes. In the case of read commands, a selected location is read and the data is transmitted to the external portions of the speech processor via the back-telemetry (BT) link. This block outputs the read- and write-enable signals to the rest of the ICS2.

The Datapath Block 327 generates the digital representation of the stimulus signals, which are then output to the DAC block 328. The Datapath is a programmable state-machine that generates repetitive waveforms on 16 channels. These waveforms are amplitude-modulated by data that is supplied on a real-time basis by the external portions of the speech processor. The Datapath Block 327 is further broken down into the Amplitude Buffer 340, the Datapath Data logic 341, the Datapath Control logic 342, and the Pulse Table RAM 344.

The Pulse Table RAM 344 controls the shape and relative timing of the stimulus signals. In the preferred embodiment, it is a 256-word-by-18-bit block of memory. Each word in the table defines one output transition for one of the 16 DACs included in the DAC block 328. Various fields in the Table address the particular DAC, provide a read address for the Amplitude Buffer, control arithmetic and logic functions on the stimulus data, and provide sequence control for the state machine. The Pulse Table 344 is written by the external portions of the speech processor prior to the start of stimulation.

The Amplitude Buffer 340 is smaller memory (32 by 9) that stores the audio-derived amplitude data received through the external or remote portions of the speech processor. Amplitude data is in the form of 9-bit sign-magnitude words, and is organized into frames of up to 16 words each. The Amplitude Buffer 340 double-buffers the data, receiving a one frame while the Pulse Table 344 addresses the previous frame.

The Datapath Data block 341 performs various arithmetic and logic functions on the amplitude data and outputs the signed, 11-bit result to the DACs within the DAC block 328.

The Datapath Control block 342 controls the overall timing for a state machine, which state machine provides the basic control for the ICS2. This logic is driven by the 1.11 MHz system clock, and so all stimulus timing is based on a programmable time interval, which is an integral number of system clock periods. This logic generates the read address for the Pulse Table RAM 344 and the write address for the Amplitude Buffer 340.

The DAC Block contains 16 11-bit current mode DACS that drive the stimulation electrodes. The DACs are bipolar, so they each sink or source current depending on the state off the sign bit. The main operating specifications for the each DAC are as follows:

Input: 11-bit sign-magnitude data
Output Current Ranges: 0–255 uA, 0–510 uA, 0–1020 uA, 0–2040 uA (current range is programmed globally.)
Rise Time: <1 usec to 66% point with 10 Kohm load.
Setting Time: <3 usec
Minimum Pulse Width: 10 usec
Compliance voltage: +/−3.3–8V relative to $V_G$. as determine by $V_P$ level. In addition, each DAC input is double buffered so that DAC outputs can be updated simultaneously after the Datapath data logic 341 sequentially sets up the next value for each channel. A more detailed description of the DAC's used within the DAC Block 328 may be found in copending patent application Ser. No. 60/090,833, filed Jun. 26, 1998, which application is assigned to the same assignee as is the present application, and which application is incorporated herein by reference.

Still with reference to FIG. 1C, the Discharge Control block 329 allows a discharge resistor to be programmably connected to each stimulation electrode in order to drain off any charge unbalance. The following resistor values are available:

None (open)
150 Kohm
300 Kohm
150K‖300 Kohm

In addition to the discharge resistors (which are programmed statically), this block 329 also contains switches to dynamically short each electrode to analog ground ($V_G$), under control of the pulse table and/or the amplitude data from the external speech processor.

The Stapedius/Indifferent Electrode Control block 330 contains switches that can programmably connect the Indifferent and Stapedius Electrodes to analog ground ($V_G$).

The voltmeter block 331 contains the measurement and monitoring circuitry that is the focus of the present invention, and is explained in greater detail below in connection with the description of FIGS. 2, 3 and 4. Such circuitry block 331 contains an analog-to-digital converter (ADC) 350 along with analog multiplexors 351, 352 and a high-gain amplifier 353. The circuitry within block 331 digitizes potentials present on the ceramic hybrid 306 as well as internal power supply voltages. Typically, circuit block 331 is used for three basic functions:

(1) monitoring of power supplies during normal operation;
(2) measurement of electrode impedance during fitting; and
(3) measurement of evoked neural response to applied stimulus for fitting, research and control purposes.

The "A/B" multiplexor 351 of the voltmeter block 331 advantageously may select any of the electrodes as sources for the differential inputs of the amplifier 353. The amplifier 353 is programmable with a gain that may be set from 1 to 1000, and is designed for recovery of input overloads, to facilitate the measurement of low-level neural response signals following a stimulus pulse. The "C" multiplexor 352 selects between the output of the amplifier 353 or the power supply voltages as inputs to the ADC 350.

The ADC 350 has a 9-bit twos-complement output, with programmable sampling rates of 60 Khz, 30 Khz, and 10 Khz. Combined with the amplifier gain, the ADC 350 can resolve input signals as small as 10 uV. The ADC output can either read directly over the back-telemetry link (in the case of a single-sample capture), or can be automatically stored in unused locations in the Pulse Table RAM 344. In the latter case, the RAM contents would be read back over the BT link after the capture has completed.

Still with reference to FIG. 1C, it is noted that the Implant Identification block 332 provides a 16-bit ID number that is unique to each ICS2, to support tracking and calibration functions in software. The ID number is assigned by means of bond wires on the hybrid during manufacture The Parallel-to-Serial Converter 333 takes the 9 bits of BT data generated by a read command and serializes it, adding start, top and parity bits. The resulting 111 Mbit/sec NRZ serial data stream goes to the driver electronics of the BT Oscillator/Driver circuit 334 for transmission to the external portions of the speech processor.

The BT Oscillator/Driver circuit 334 takes the 123 Mbit/sec BT serial data stream output from the Parallel to Serial Converter 333 and outputs an FSK modulated signal with a 10.7 Mhz carrier, which drives the back telemetry coil 304.

The Error and Stimulation Control block 335 enables stimulation, and monitors various error signals from the rest of the ICS2. Various responses to errors may be programmably selected.

Figures 1, 1C, 2:
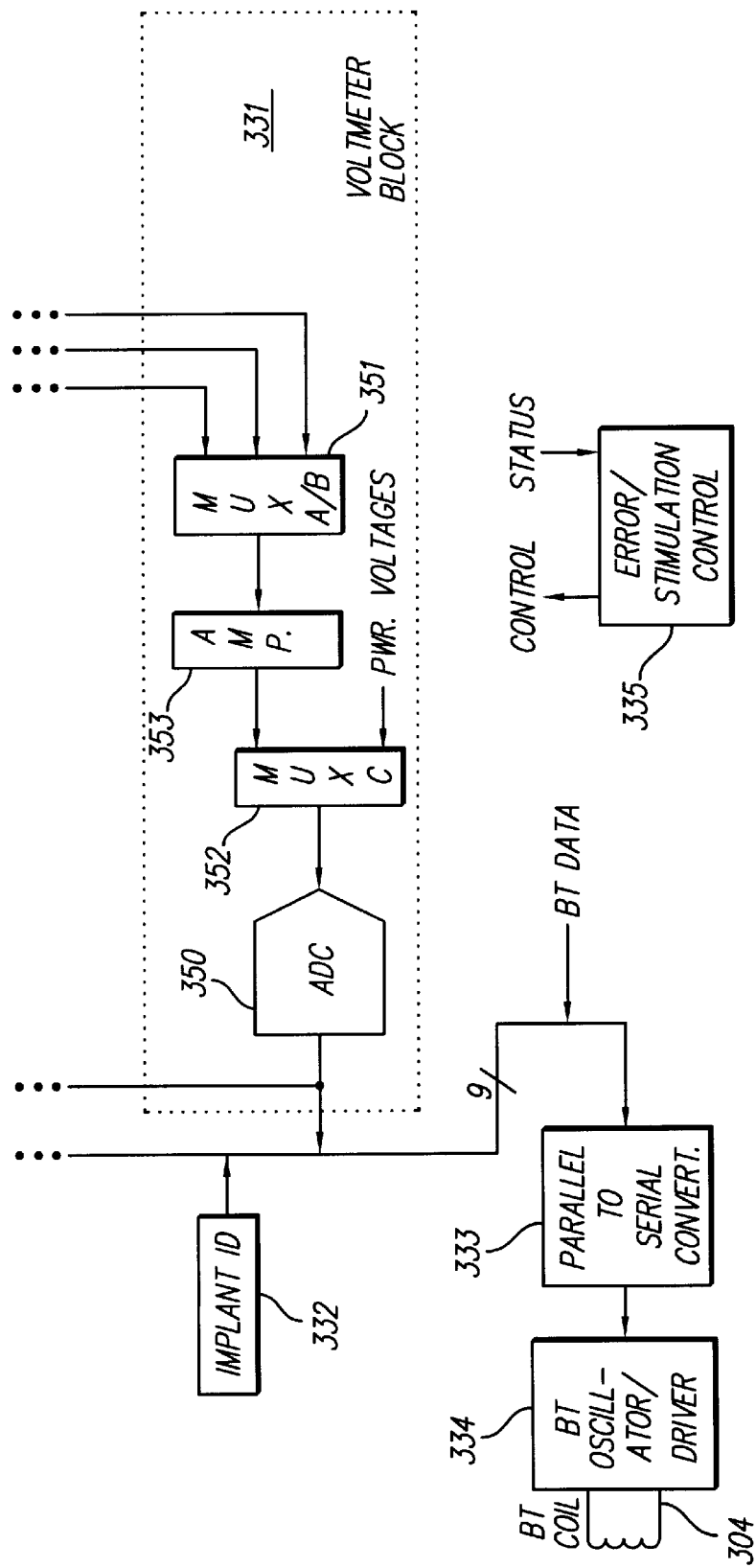
FIG. 2 is a functional block diagram of the back telemetry portion of a tissue stimulator wherein the present invention is employed.
Figure 2:
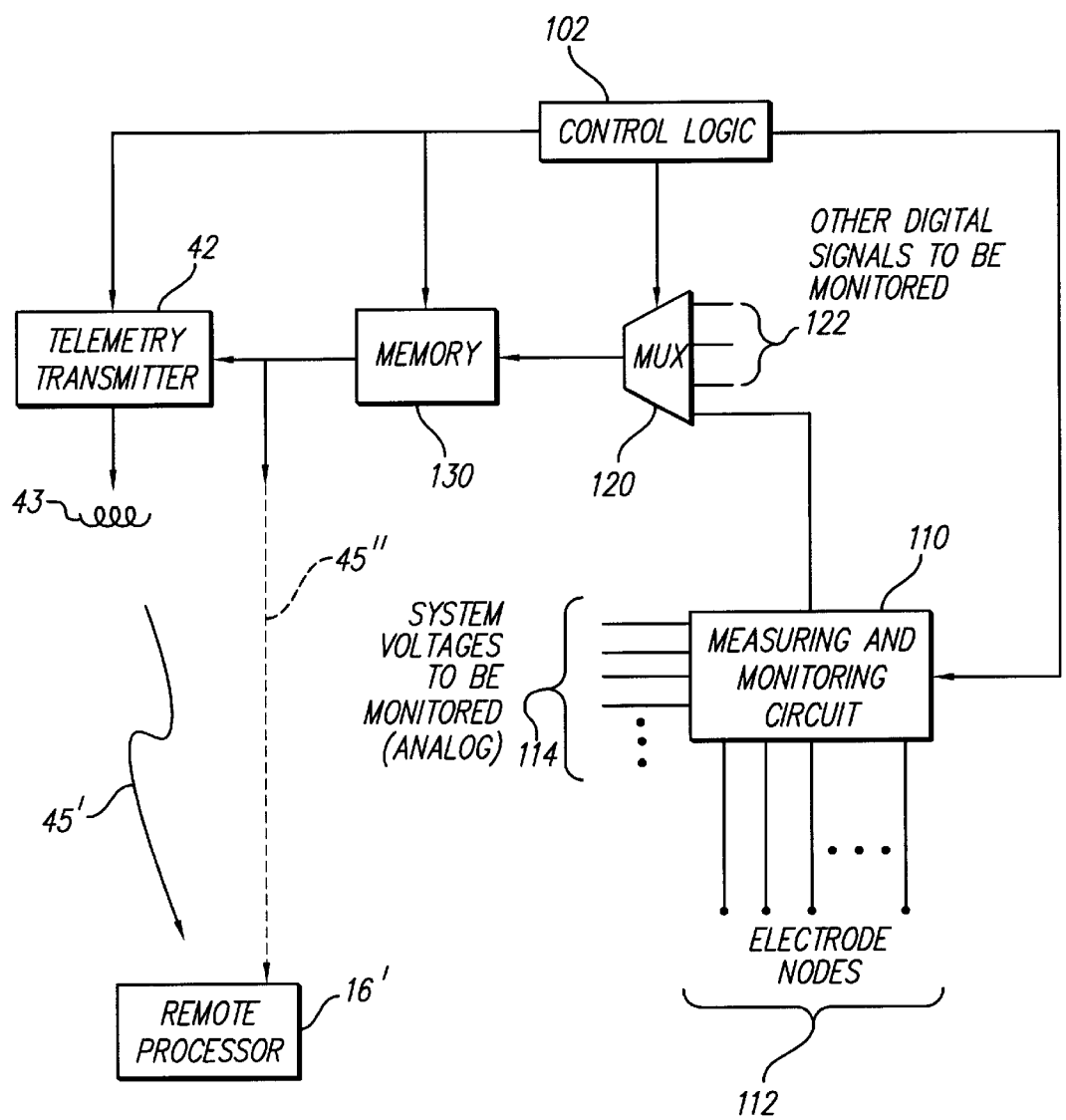

Turning next to FIG. 2, there is shown a functional block diagram of one embodiment of the back telemetry portion of an ICS system of the type with which the present invention is used. Such embodiment includes control logic 102 (which may comprise state logic and/or part of the overall control logic used within the ICS or ICS2, and which may, in a preferred embodiment, be implemented using one of more microprocessors). The control logic 102 generates all of the control signals, e.g., control inputs 172 (see FIG. 3), used by the invention in order to allow it to achieve the desired control and timing needed to monitor and process the signals as described below.

At the heart of the present invention is a measuring and monitoring circuit 110, described in more detail below in FIGS. 3 and 4. The measuring and monitoring circuit 110 includes the circuitry associated with the voltmeter block 331 and data path block 327 (described above in FIG. 1C) and whatever other circuitry is needed to interface with all of the nodes and other locations within the ICS2 were desired parameters may be present or measurable. Included are a multiplicity of electrode nodes 112, each of which connects with an electrode. The electrodes may be included within a cochlear electrode array, attached to the middle ear so as to sense the stapedius reflex, or connected to other desired stimulation or reference points. For example, a reference (indifferent) electrode may be connected to the case of the ICS2. In a preferred embodiment, there are twenty electrodes connected to the measuring and monitoring circuitry 110: sixteen stimulating electrodes, two stapedius electrodes, and two indifferent electrodes.

A multiplicity of system voltages and/or other analog signals 114 that may be monitored by the invention are also connected to the measuring and monitoring circuitry 110.

It is the primary function of the measuring and monitoring circuitry 110 to select one of the analog signals for monitoring, or a pair of the electrodes (which can then be used as sense electrodes), and process the signal present by virtue of the selection, e.g., amplify it, attenuate it, filter it, etc., as required, and present such selected signal as a digitized signal to a digital multiplexer (MUX) 120. The digital MUX 120, in turn, as controlled by the control logic, allows the signal to be stored in memory 130, as required, and then sent through the telemetry transmitter 42 to a remote processor 16'. Here, it is to be emphasized that the term "remote", when used to described the processor 16', does not necessarily mean that the processor 16' is external, or non-implanted. The remote processor 16' may comprise part of the external portion of the stimulation system, e.g., part of the wearable system 10 shown in FIG. 1. For that reason, FIG. 2 shows the telemetry transmitter 42 sending its signal, represented by wavy arrow 45', through a telemetry coil 43 to the remote processor 16'. However, it is to be understood that the remote processor 16' may also comprise part of any system, whether implanted or not, that is coupled to and/or cooperates with, the operation of the ICS or ICS2. Thus, for example, the remote processor 16' may actually receive its signal directly from the memory 130, over alternate signal line 45", in those instances where the remote processor comprises circuitry housed within the same hermetically sealed case as the stimulator. In other instances, the remote processor 16' may be housed within a separate housing, which separate housing may be implanted, as taught e.g., in U.S. patent application No. 09/126,615, filed Jul. 31, 1998, or application Ser. No. 60/108,923, filed Nov. 17, 1998, previously incorporated herein by reference. Alternatively, such separate housing may be part of an external or wearable portion, as shown in FIG. 1, in which case the remote processor 16' shown in FIG. 2 may actually comprise the wearable processor 16 shown in FIG. 1. Thus, it is seen that the "remote processor" 16' may be implanted within the same case as the stimulator circuitry, implanted within a separate case coupled to the stimulator case, or external (non-implanted).

As required, e.g., during a fitting session, the WP 10 (see FIG. 1) may be augmented by, or replaced with, a personal computer (PC) programmed to aid in the processing of the signals received from the ICS, and/or in the generation of the signals to be applied to the ICS. Through such augmentation or substitution, it is thus seen that the signals monitored and/or measured by the measuring and monitoring circuit 110 (FIG. 2) may also be sent to such external PC through the telemetry transmitter 42. Advantageously, being able to send signals that have been sensed through selected ones of the various electrode nodes to an external PC in this manner affords a very valuable and useful research tool.

As seen in FIG. 2, other digital signals 122 from within the ICS or ICS2 may also be coupled through the MUX 120 to the memory 130. Once stored in memory 130, such signals may be retrieved at an appropriate time and rate for analysis, or for use by other portions of the system.

Figure 3:
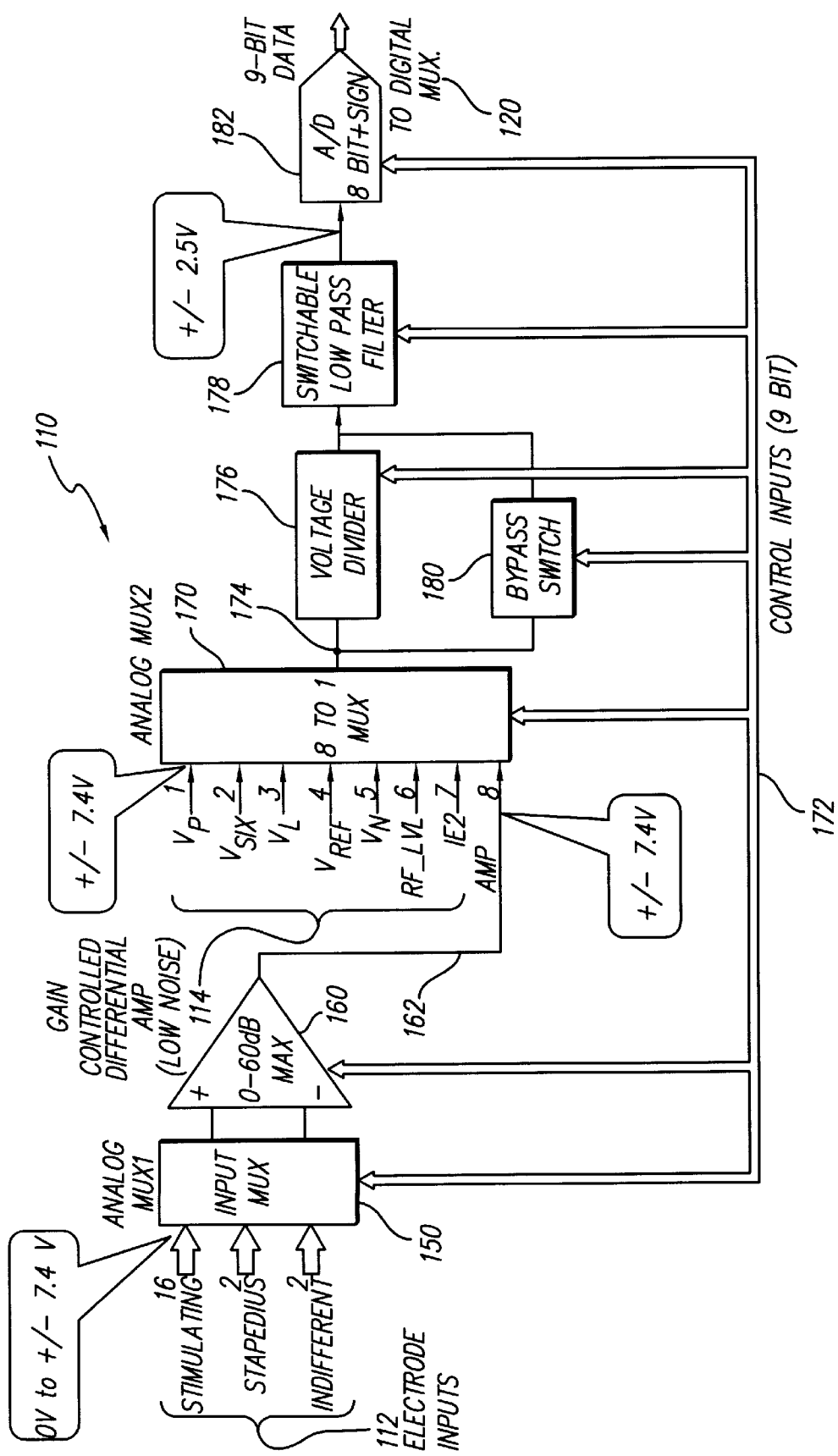
FIG. 3 is a block diagram of the measuring/monitoring circuit of the present invention.

Turning next to FIG. 3, a functional diagram of the measuring and monitoring circuit 110 of the present invention is illustrated. The circuitry 110 allows any pair of electrodes 112 to be used as "sense" electrodes. In the preferred embodiment, these sense electrodes 112 may be selected from 16-stimulating electrodes, 2-stapedius electrodes, or 2-indifferent (reference) electrodes by an input analog multiplexer (Input MUX) 150. The signal sensed by the sense electrodes is differentially amplified in a gain-controlled, dc coupled, differential amplifier 160. The output 162 of the differential amplifier 160 is applied to the input of a second analog MUX 170. Other analog inputs 114 are also applied to the input of the MUX 170.

The MUX 170, as controlled by control bits 172 obtained from the control logic 102 (FIG. 2), selects one of the analog inputs and connects it to its output node 174. A voltage divider 176 connects the node 174 to a switchable low pass filter 178. The low pass filter 178 is used to filter out any high frequency components, e.g., switching transients or glitches, that may be present in the selected analog signal.

The voltage divider 176 functions as an attenuator to help keep the amplitude of the selected signal within a desired range. Such attenuation is not always needed, thus an analog switch 180, also controlled by the control bits 172, shunts the voltage divider and allows the voltage divider to be selectively bypassed.

The output of the Low Pass filter 178 is applied to an analog-to-digital (A/D) converter 182. The A/D converter operates at a maximum sampling frequency. A representative sampling frequency is, .e.g., 60K samples/second (16.7 $\mu$s/sample). The digitized signal, which is preferably a 9-bit signal, is then sent to the digital MUX 120 (FIG. 2). If selected by the MUX 120, this digital signal may then be stored in random access memory (RAM) 130. Advantageously, the RAM 130 acts as a buffer, allowing the digitized sensed signal to be transmitted or sent to a remote processor 16', e.g., the external processor 16 (FIG. 1A) or other PC-based processor, via the back telemetry transmitter 42 and associated transmission link, at a slower rate than it is generated. (Note, although shown as a Digital MUX 120 in FIG. 2, such representation is functional. In practice, digital data to be sent or transmitted to a remote processor may be simply stored in a memory, e.g., memory 344, and then read out of memory word by word onto an output bus in a controlled sequence, serialized as required in a parallel-to-serial-converter 333, and transmitted bit by bit in a serial data stream by the back telemetry driver circuit 334, as illustrated in FIG. 1C.)

Advantageously, the measuring and monitoring circuit 110 may operate in at least two power modes. For frequent monitoring of the other analog signals 114, which analog signals typically comprise voltages and other reference signals used within the ICS, the MUX 150 and differential amplifier 160 may be turned OFF, thereby conserving power. For less frequent monitoring of electrode-related signals, e.g., electrode impedances, evoked responses, and the like, the MUX 150 and differential amplifier are turned ON. In this manner, only the circuitry needed for whatever function is being performed at the moment is turned ON, with the other un-needed circuitry (at the moment) being turned OFF.

One of the key advantages of the measuring and monitoring circuitry 110 of the present invention is its ability to measure an evoked response from an applied stimulus. In order to measure an evoked response, it is first necessary to apply a stimulus to a selected electrode pair so that an evoked response will occur. The present invention advantageously allows any two electrodes to be used as stimulus electrodes and any two electrodes to be used as sense electrodes. A stimulus is applied to a selected pair of electrodes using the output circuitry of the ICS2, e.g., the DAC circuitry 328 (FIG. 1C).

In order to use the measuring and monitoring circuit 110 to measure an evoked response, a stimulus signal is applied to a selected pair of the sixteen stimulating electrodes in a bipolar or monopolar manner. If a monopolar stimulating mode is selected, one of the sixteen stimulating electrodes is paired with one of the indifferent (reference) electrodes. If a bipolar stimulating mode is selected, then two of the sixteen stimulating electrodes (typically adjacent electrodes) are selected as a stimulus pair.

Figure 4:
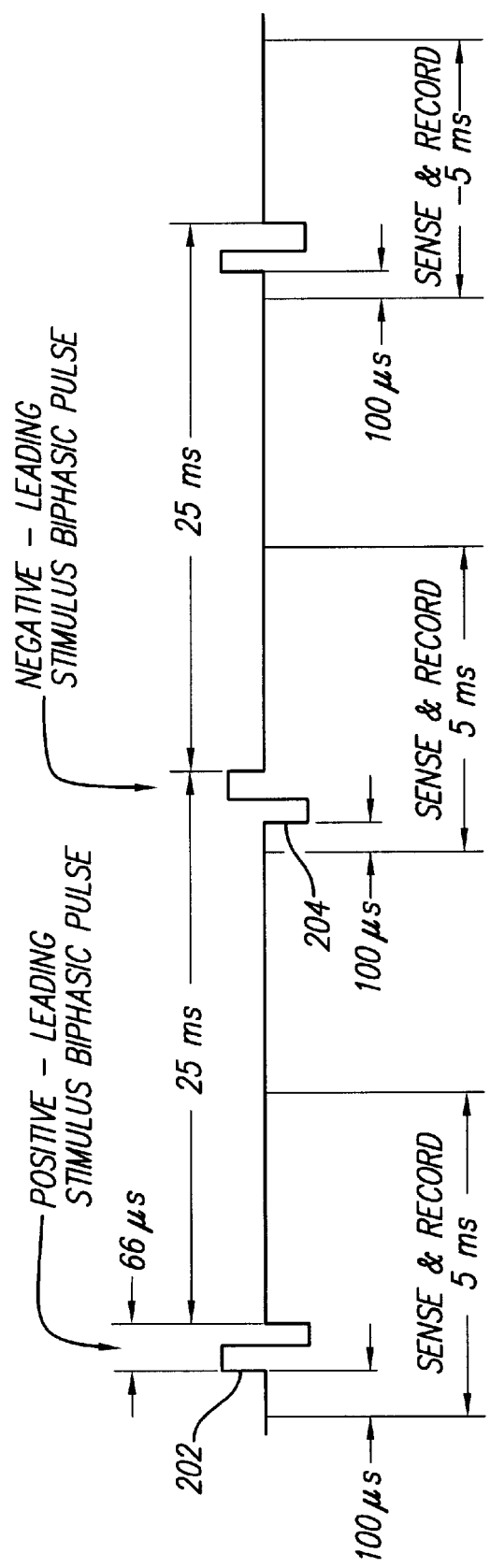
FIG. 4 is a timing diagram illustrating operation of the circuit of FIG. 3 when used to measure an evoked response.

The preferred timing that is used when applying the stimulus and sensing the response during operation of the measuring and monitoring circuit 110 is shown in FIG. 4. As seen in FIG. 4, a biphasic pulse 202 has a leading edge of one polarity and a trailing edge of the opposite polarity. The biphasic pulse preferably has a total width no greater than about 80 $\mu$s, e.g., has a width of about 66 $\mu$s, and has a repetition rate less than about 50 Hz, e.g., a repetition rate of about 40 Hz (i.e., has a period of about 25 ms). A train of such biphasic pulses is applied to the selected stimulus pair of electrodes.

The stimulating biphasic pulse train may comprise either positive-leading stimulus biphasic pulses or negative-leading stimulus biphasic pulses. A positive-leading stimulus biphasic pulse is one wherein the first half of the biphasic pulse is a positive pulse and the second half is a negative pulse; i.e., the biphasic pulse has a positive-negative polarity (the leading pulse of each biphasic pulse has a polarity which is positive relative to the trailing pulse). A negative-leading stimulus biphasic pulse is one wherein the first half of the biphasic pulse is a negative pulse and the second half is a positive pulse, i.e., the biphasic pulse has a negative-positive polarity (the leading pulse of each biphasic pulse has a polarity which is negative relative to the trailing pulse). Examples of both types of biphasic pulses are shown in FIG. 4, where the biphasic pulse 202 illustrates a positive-negative polarity, and the biphasic pulse 204 illustrates a negative-positive polarity. Preferably, the biphasic pulse train implements an alternating polarity, e.g., the pulses in the pulse train alternate between a positive-negative polarity and a negative-positive polarity, as shown in FIG. 4. Using an alternating polarity for the biphasic stimulation pulses in this manner allows the response signal to be averaged, which averaging effectively cancels out undesirable portions of the evoked response. Other pulse configurations, e.g., using multiphasic pulses in the pulse train, may also be used for this purpose.

As seen in FIG. 4, about 100 $\mu$sec before the leading edge of the stimulus pulse, the Input MUX 150 (FIG. 3) selects the sensing electrode pair and connects it to the differential amplifier 160 so that the amplifier 160 can monitor whatever signal appears on the electrodes of the pair. The response signal that is sensed includes both the artifact associated with the stimulus and the evoked response. Monitoring of the sensed electrodes continues for about 5 ms following each stimulus. The signal monitored through the selected sense electrode pair, as indicated above, is passed through the switchable low pass filter 178 (if necessary), digitized in A/D converter 180, stored in RAM 130, and eventually transmitted back to the remote processor 116, or remote PC. The external processor or remote PC then uses appropriate software-controlled processing techniques to remove the artifact.

During sensing, in the presence of the large artifact, the gain of the differential amplifier is controlled appropriately so that it operates in a linear range. This allows the amplifier to operate rapidly, without the need to blank out the artifact, e.g., by open circuiting the sense electrodes. Thus, it is seen that the design philosophy associated with the measuring and monitoring circuit 110 is to accurately sense and record all signals that are sensed by the sensing electrodes during the entire monitoring period, e.g., for the entire 5 milliseconds, commencing a short time, e.g., about 100 $\mu$sec, before the stimulus is applied. Such sensed and recorded signals may then be subsequently analyzed and/or processed, e.g., using appropriate processing circuitry and/or software, contained within a remote processor, in order to eliminate the artifact and other undesirable signals.

Figure 5:
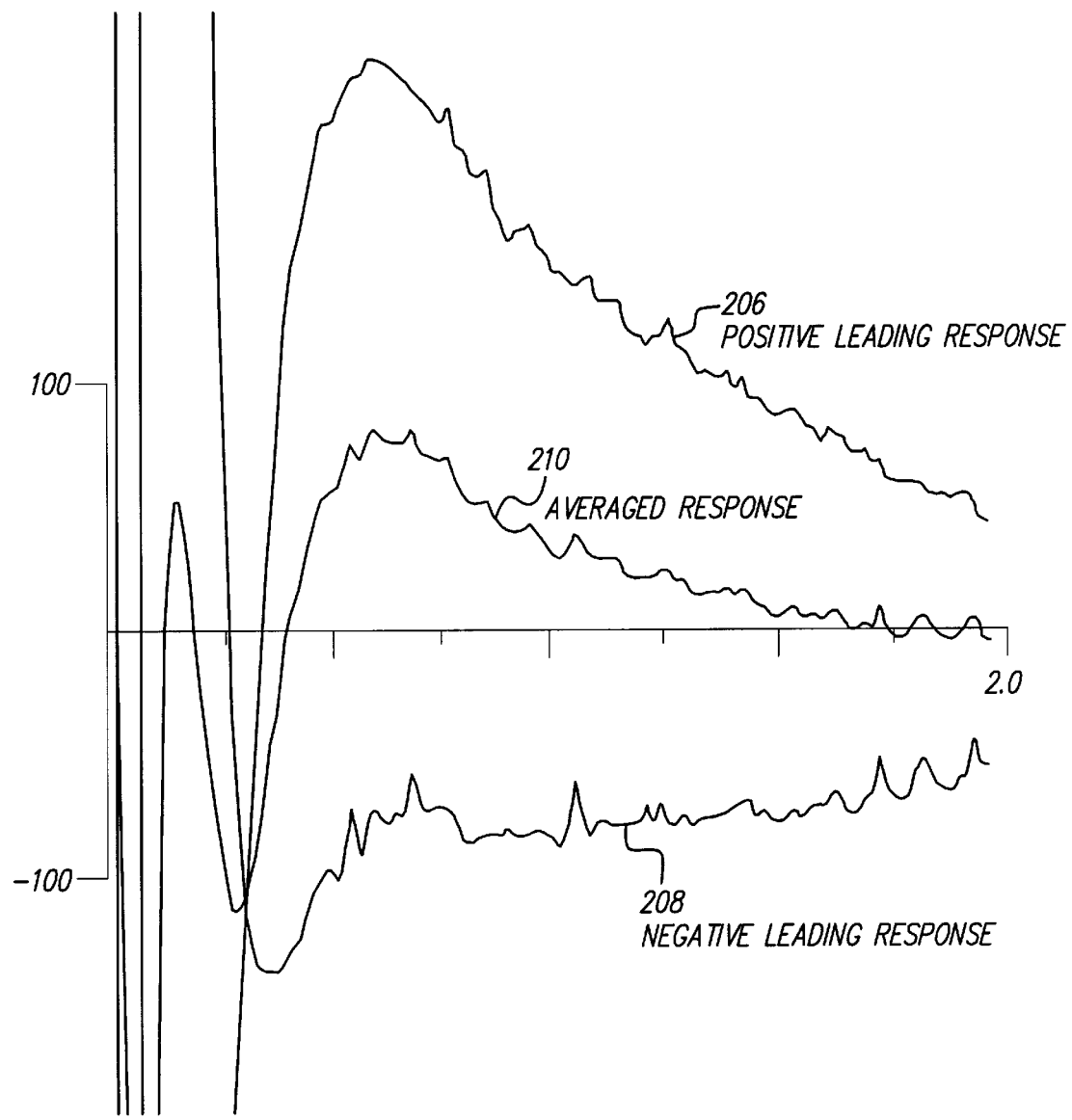
FIG. 5 is a waveform diagram illustrating a preferred technique used within a remote processor to extract the evoked response from the signals detected using the circuit of FIG. 3 when controlled using the monitoring and timing approach illustrated in FIG. 4.

An illustration of a preferred processing technique for sensing the evoked response is depicted in the waveform diagram of FIG. 5. The waveforms shown in FIG. 5 represent an actual reconstruction of analog waveforms, displayed on an oscilloscope or other equivalent instrument, obtained from the digital data sent to a remote processor from measuring and monitoring circuitry 110 of the type shown in FIG. 3. The vertical axis in FIG. 5 represents voltage, and is marked with a "100" at ±100 microvolts. The horizontal axis represents time, and is marked by a "2" at the 2 millisecond point. Thus, FIG. 5 shows the sensed signals that occur on the selected pair of sense electrodes for the first two milliseconds following application of a stimulus pulse. The sensed signals may be monitored for whatever time is needed, e.g., from 2–20 milliseconds. Note, in FIG. 4, the signals are monitored for a sense and record window that is 5 milliseconds long.

A first waveform 206 in FIG. 5 represents the response to a first biphasic pulse having a positive-negative polarity, e.g., like the pulse 202 shown in FIG. 4. A second waveform 208 in FIG. 5 represents the response to a second biphasic pulse having a negative-positive polarity, e.g., like the pulse 204 in FIG. 4. In accordance with a preferred processing technique, the response to the positive-negative pulse, i.e., the waveform 206, is averaged with the response to the negative-positive pulse, i.e., the waveform 208, producing an evoked potential response. To improve the signal-to-noise ratio of the evoked potential response, two or more responses are averaged, i.e., two or more waveforms of the type shown as waveform 206 are averaged with two or more waveforms of the type shown as waveform 208. Each time two responses—one from a positive-negative biphasic stimulus and one from a negative-positive biphasic stimulus—are added to the average, the signal-to-noise ratio improves. An evoked potential response waveform 210 results. The response waveform 210 shown in FIG. 5 represents the result of fifty such averages.

Once the evoked potential response waveform 210 has been obtained, it may be used for various purposes. For example, the evoked potential may be used in an automatic calibration routine wherein the stimulus levels of the currents applied to the stimulus electrodes through the DAC blocks 328 (FIG. 1C) are dynamically adjusted until a desired evoked response occurs. The evoked response could, of course, also be used in a manual calibration routine as part of a fitting process wherein the stimulus levels are manually set based on objective data contained within the evoked potential signal (as opposed to subjective data which is commonly used now during a fitting procedure). Alternatively, the evoked potential may be used for research purposes, e.g., to achieve a better-understanding of the neuro-physiology of the ear.

It is noted that the selected sense electrodes will typically be different than the stimulus electrodes. Both the sensing electrodes and the stimulus electrodes may be configured as monopolar pairs (one electrode plus a reference electrode), or bipolar pairs (two electrodes, typically adjacent electrodes).

Advantageously, the invention may also be used to measure an electric field (voltage) associated with a stimulus electrode or a stimulus electrode pair. In such instance, the sensing electrodes may be the same as the stimulus electrodes. Or, alternatively, a stimulus may be applied to a selected pair of stimulus electrodes, and the electric field (voltage) at others of the electrodes (sensing electrodes) at the time the stimulus is applied, and known time increments for a few milliseconds thereafter, can be measured and saved. The particular electrodes used as the sensing electrodes can be altered or changed as often as necessary, e.g., in between application of the stimulus, and in this manner the electric field (voltage) that is present at all, or most all, of the other electrodes can be determined in response to the applied stimulus, for several milliseconds after application of the stimulus, thereby allowing the electric field distribution (voltage gradients) around the various electrodes as a function of time to be determined, analyzed and studied. Such electric field distribution information has proven to be extremely valuable as a research, analytical and fitting tool in characterizing and quantifying the electric fields that are created through application of stimuli of various magnitudes to different ones of the stimulus electrodes.

In a preferred embodiment, the amplifier 160 (FIG. 3) that differentially amplifies the sensed signals preferably comprises a seven stage, dc coupled, amplifier having a maximum gain of about 60 dB. Six of the amplifier stages are used to amplify and buffer the signal. A seventh amplifier stage is used for nulling the amplifier. Nulling occurs using one of two methods. In a first method, nulling is performed in between signal sensing, i.e., after the 5 ms sensing window has occurred. In a second method, nulling occurs continuously at low frequencies (dc to about 150 Hz).

As described above, it is thus seen that the present invention provides a way of sensing evoked potentials between a selected pair of electrodes. More particularly, it is seen that when sensing the evoked potential, the gain setting of a differential, fast-recovery, amplifier connected to the selected pair of sensing electrodes is controlled to operate in a linear region for the signals of interest. In this way, there is no need to blank the signal path during application of the stimulus, thereby avoiding switching transients or signal glitches that could easily be mistaken for bio signals.

It is also seen that the invention, when operating in an electrode-related measurement mode, allows any two electrodes, including one or more reference electrodes, to be paired together in order to make a desired differential measurement between the selected pair of electrodes.

As further described above, it is seen that when measuring evoked potentials between the selected pair of electrodes, the present invention may use a stream of biphasic stimulus pulses having alternating positive leading and negative leading phases. Application of such stimulus allows the resulting response to be averaged, e.g., using a remote processing device, in a way that cancels out induced signals, leaving the desired bio signals for analysis.

Thus, it is seen that the invention provides a measurement/monitoring circuit for use within an implantable stimulator that facilitates sensing the evoked response to an applied stimulus.

It is further seen that the invention provides such a measurement/monitoring circuit that is programmable, allowing any of a variety of types of signals and/or measurements to be made, including selective pairing of electrodes through which evoked or other electrode-related measurements are to be sensed.

Additionally, it is seen that the invention provides a measurement/monitoring circuit for use within an implantable stimulator that operates at minimal operating power.

While the invention herein disclosed has been described by means of specific embodiments and applications thereof, numerous modifications and variations could be made thereto by those skilled in the art without departing from the scope of the invention set forth in the claims.

What is claimed is:

1. In an implantable stimulator having a multiplicity of electrodes and means for applying a stimulus to a selected pair of said electrodes, forward control means for controlling the stimulator from a remote controller, and backward monitoring means for sending signals from the implantable stimulator to the remote controller, a circuit for measuring and monitoring an evoked response resulting from the application of a stimulus to the selected pair of stimulus electrodes, comprising:

a first multiplexer connected to the multiplicity of electrodes that selects a desired pair of said electrodes as a sensing pair of electrodes;

a differential amplifier connected to the first multiplexer for amplifying a signal received through the sensing pair of electrodes to create an amplified sensed signal, said differential amplifier having a programmable gain;

a second multiplexer that selects one of a plurality of analog signals, including said amplified sensed signal, and presents said selected analog signal to an output signal port;

an analog-to-digital (A/D) converter coupled to the output signal port of the second multiplexer that digitizes signals appearing on the output signal port to create a digitized sensed signal;

a memory that stores the digitized sensed signal, wherein said memory is coupled to the backward monitoring means;

wherein data stored in the memory, including the digitized sensed signal, may be sent to the remote controller through the backward monitoring means.

2. The evoked response measuring circuit of claim 1 further including analog signal processing means switchably interposed between the output signal port of the second multiplexer and the A/D converter.

3. The evoked response measuring circuit of claim 2 wherein the analog signal processing means interposed between the output signal port of the second multiplexer means and the A/D converter comprises a low pass filter.

4. The evoked response measuring circuit of claim 2 further including attenuator means interposed between the output signal port of the second multiplexer means and the analog signal processing means for attenuating signals on the output signal port.

5. The evoked response measuring circuit of claim 4 wherein said attenuator means comprises a voltage divider circuit.

6. The evoked response measuring circuit of claim 4 further including bypass means for selectively bypassing said attenuator means so that signals appearing on the output signal port are not attenuated.

7. The evoked response measuring circuit of claim 6 wherein said bypass means for selectively bypassing the attenuator means comprises an analog switch shunting said attenuator means, which analog switch, when turned ON, provides a signal path around said attenuator means.

8. An implantable stimulator comprising:
a multiplicity of electrodes;
means for applying a stimulus to a selected pair of said electrodes, the selected pair of said electrodes comprising stimulus electrodes;
memory means for storing signal data;
transmission means for sending the signal data stored within the memory means to a remote processor; and
a measuring/monitoring circuit comprising:
first selection means for selecting a pair of sensing electrodes from among the multiplicity of electrodes,
a differential amplifier connected to amplify signals present on the sensing electrodes and produce an amplified output signal,
second selection means for selecting one of a multiplicity of analog signals, including the amplified output signal produced by the differential amplifier, and presenting said selected analog signal on an output port,
an analog-to-digital (A/D) converter connected to the output port of the second selection means, the A/D converter including digitizing circuitry that digitizes analog signals present on the output port to create a digitized signal, and wherein the A/D converter is coupled to the memory means, whereby the digitized signal may be stored in the memory means and sent as signal data to the remote processor.

9. The implantable stimulator of claim 8 further including a low pass filter interposed between the second selection means and the A/D converter, whereby the selected analog signal selected by the second selection means passes through the low pass filter prior to being presented to the A/D converter.

10. The implantable stimulator of claim 9 further including means for selectively attenuating the selected analog signal prior to presenting said signal to the A/D converter.

11. The implantable stimulator of claim 10 wherein said means for selectively attenuating the selected analog signal comprises a voltage divider circuit interposed between the second selection means and the low pass filter.

12. The implantable stimulator of claim 11 further including an analog switch shunting said voltage divider circuit, wherein said analog switch is controlled by said control means to selectively provide a signal path that bypasses the voltage divider circuit.

13. The implantable stimulator of claim 9 wherein said control means includes means for selecting the pair of sense electrodes a first prescribed period of time prior to application of the stimulus to the stimulus electrodes.

14. The implantable stimulator of claim 13 wherein said control means further selects the pair of sense electrodes for a second prescribed period of time following application of the stimulus to the stimulus electrodes.

15. The implantable stimulator of claim 14 wherein the stimulus applied to the stimulus electrodes by the stimulus application means comprises a stimulus pulse having a duration of less than about 100 microseconds ($\mu$s), and wherein the second prescribed period of time during which the sensing electrodes are selected following application of the stimulus comprises at least 5 milliseconds.

16. The implantable stimulator of claim 15 wherein the stimulus applied to the stimulus electrodes by the stimulus application means comprises a stream of stimulus pulses which are applied to the stimulus electrodes at a pulse rate no greater than about 50 pulses per second.

17. The implantable stimulator of claim 16 wherein the stream of stimulus pulses comprises a stream of biphasic stimulation pulses, each biphasic pulse having a first phase of a first polarity followed by a second phase of the opposite polarity.

18. The implantable stimulator of claim 17 wherein the first and second phases of each biphasic pulse each have a duration no greater than about 40 $\mu$s, and wherein the second phase immediately follows the first phase, making the total duration of each biphasic pulse no greater than about 80 $\mu$s.

19. The implantable stimulator of claim 17 wherein the polarity of the biphasic pulses alternates from one polarity to the other polarity from one biphasic pulse to the next biphasic pulse within the stream of biphasic pulses.

20. The implantable stimulator of claim 13 wherein the differential amplifier recovers quickly and symmetrically from saturation and includes a programmable gain adjustment which, when adjusted, sets the gain of the amplifier as a function of control signals, and wherein the gain of the differential amplifier is set by the programmable gain adjustment to operate in a linear region for the signal being monitored.

* * * * *